United States Patent [19]
Wilk et al.

[11] Patent Number: 5,282,788
[45] Date of Patent: Feb. 1, 1994

[54] METHOD AND DEVICE FOR OBTAINING CONTINUED TRANSDERMAL ACCESS

[76] Inventors: Peter J. Wilk, 185 W. End Ave., New York, N.Y. 10023; Naomi L. Nakao, 303 E. 57th St., New York, N.Y. 10022

[21] Appl. No.: 853,987

[22] Filed: Mar. 20, 1992

Related U.S. Application Data

[63] Continuation-in-part of Ser. No. 841,802, Feb. 26, 1992, Pat. No. 5,232,440.

[51] Int. Cl.$^5$ ............................................. A61M 31/00
[52] U.S. Cl. ..................................... 604/49; 604/164; 604/175; 604/264; 604/281
[58] Field of Search .................. 604/27, 28, 48, 49, 604/73, 93, 104–106, 158, 161, 164–166, 174–175, 264, 278, 281

[56] References Cited

U.S. PATENT DOCUMENTS

| | | | |
|---|---|---|---|
| 2,770,236 | 11/1956 | Utley et al. | 604/166 |
| 3,483,859 | 12/1969 | Pittman . | |
| 4,431,426 | 2/1984 | Groshong et al. | 604/280 |
| 4,638,803 | 1/1987 | Rand . | |
| 4,810,244 | 3/1989 | Allen | 604/44 |
| 5,085,631 | 2/1992 | Leighton | 604/28 |
| 5,106,376 | 4/1992 | Mononen et al. | 604/164 |
| 5,112,310 | 5/1992 | Grobe | 604/175 |
| 5,158,545 | 10/1992 | Trudell et al. | 604/53 |
| 5,171,226 | 12/1992 | McCrory | 604/164 |

FOREIGN PATENT DOCUMENTS

| | | |
|---|---|---|
| 2659440 | 7/1977 | Fed. Rep. of Germany . |
| 3837779 | 5/1989 | Fed. Rep. of Germany . |

*Primary Examiner*—C. Fred Rosenbaum
*Assistant Examiner*—Corrine Maglione
*Attorney, Agent, or Firm*—R. Neil Sudol; Henry D. Coleman

[57] ABSTRACT

An assembly for use in drainage of an abscess comprises an outer tubular member provided in a distal end portion with a plurality of longitudinal slits. The distal end portion of the tubular member has a spring bias tending to form the distal end portion into a substantially spherical expanded configuration to anchor the distal end portion of the tubular member in an abscess. An inner tubular member or obturator is inserted into the outer tubular member and has a distal end provided with a cutting edge projecting from the outer tubular member. Locking components on the obturator and the outer tubular member serve to maintain the latter in a stretched out cylindrical configuration enabling insertion of the distal end portion into an abscess. A needle on the distal end of the tubular member serves to inject a quantity of anesthetic into the patient at the abscess site. A similar structure is disclosed in an intravenous catheter assembly.

11 Claims, 3 Drawing Sheets

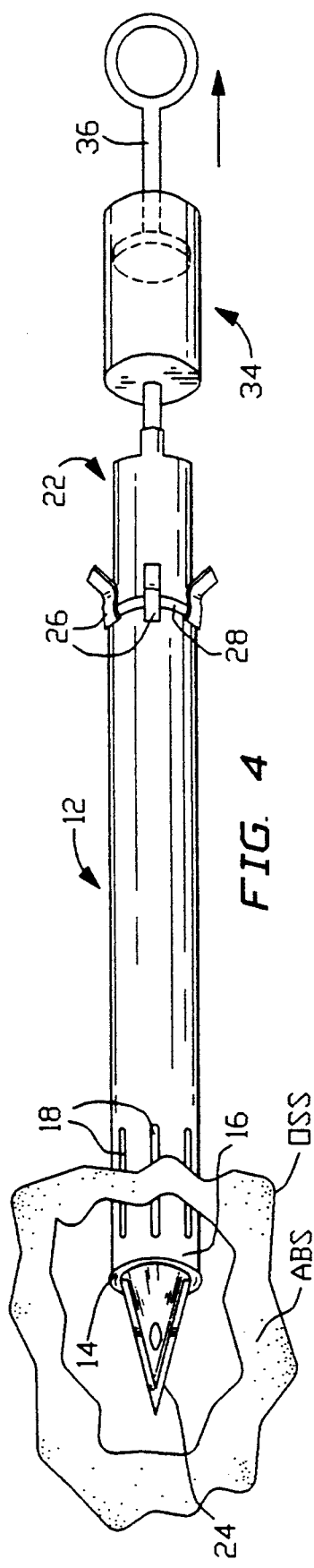
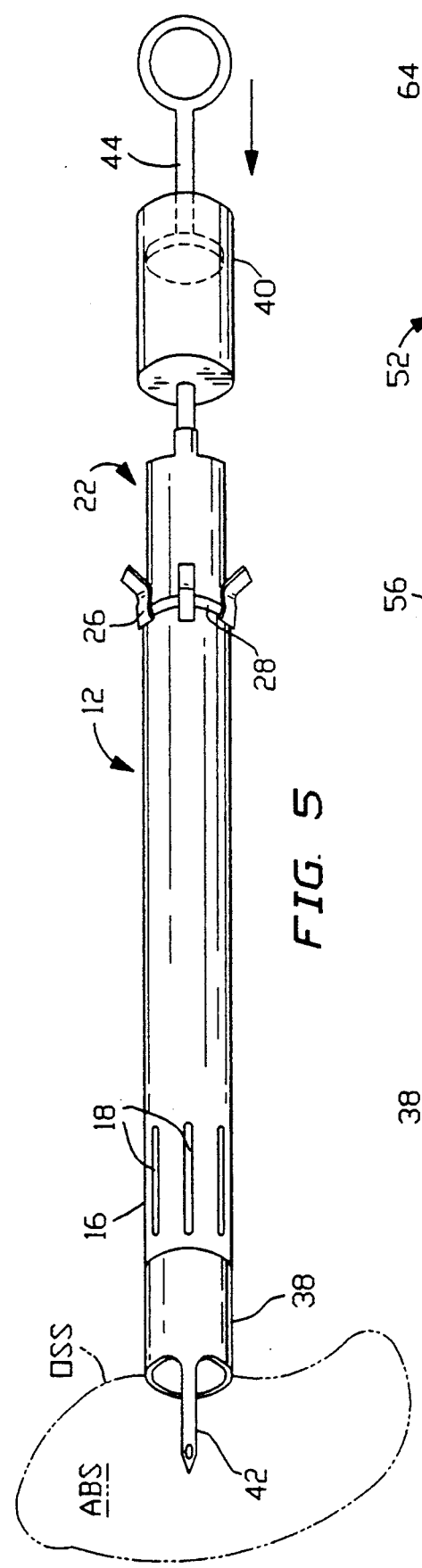
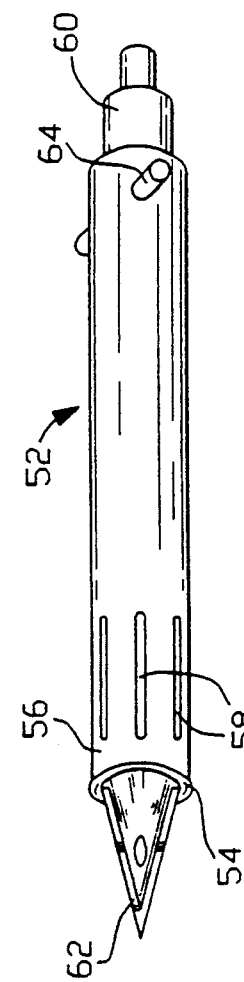

METHOD AND DEVICE FOR OBTAINING CONTINUED TRANSDERMAL ACCESS

CROSS-REFERENCE TO A RELATED APPLICATION

This application is a continuation-in-part of application Ser. No. 841,802 filed Feb. 26, 1992, now U.S. Pat. No. 5,232,440.

BACKGROUND OF THE INVENTION

This invention relates to an assembly or device for use in obtaining continued transdermal access. This invention also relates to an associated method using the device. The device and method is useful in inserting a catheter into a patient.

An abscess is a collection of pus in infected tissue and is often accompanied by inflammation or swelling. To relieve the swelling, a surgeon makes an incision through skin tissues overlying the abscess. Although some pus may be removed immediately from the abscess to reduce the swelling, fluidic matter will continue to accumulate and swelling will recur unless measures are taken to ensure continued drainage from the infected tissues.

One procedure for ensuring continued drainage of an abscess involves the use of a tubular member which is closed at a distal end, i.e., the end which is inserted by the surgeon into the abscess. Along a distal portion proximal of the closed distal tip of the tube are provided a plurality of longitudinal slits. The tube is formed at its perforated distal portion with a spring bias tending to form that portion of the tube into a substantially spherical expanded anchoring configuration wherein the slits are opened.

To insert the distal end portion of the tube into the abscess, a rod is inserted into the tube. The tube is stretched so that the distal end portion thereof assumes an elongate cylindrical configuration, rather than a spherical or expanded configuration, thereby facilitating insertion of the tube through the incision in the skin tissues overlying the abscess. Upon insertion of the distal end portion of the tube into the abscess, the tube is released so that the distal end portion assumes the spherical or expanded configuration and opens the slots to enable or facilitate continued drainage of the pus or fluidic material from the abscess.

Another situation where continued transdermal access is required is in intravenous feeding. A needle is inserted into a vein, a syringe connected to the needle being used in an aspiration technique to determine whether a vein has been properly entered by the needle. Frequently, prior to the insertion of a catheter into a vein, the point of insertion is prepared by injecting a local anesthetic with a separate needle and syringe.

OBJECTS OF THE INVENTION

An object of the present invention is to provide an improved method for inserting a catheter into a vein or into an abscess.

A more particular object of the present invention is to provide such a method which is easier and more convenient than conventional techniques.

Another object of the present invention is to provide a device or assembly which is utilizable in the improved method.

A further particular object of the present invention is to provide a device and a related method wherein a surgical procedure to insert a catheter into a vein or an abscess has fewer steps than the above-described conventional procedures.

SUMMARY OF THE INVENTION

A device for obtaining continued transdermal access to a patient comprises, in accordance with the present invention, a tubular member and a hollow inner member inserted into the tubular member, the inner member having a sharp distal end projecting from the tubular member. A syringe is connected to the inner member at a proximal end thereof, while a needle is removably attached to one of the tubular member and the inner member at a distal end thereof, whereby an ejection stroke of the syringe ejects fluid material from the syringe through the inner member and out along the needle.

According to another feature of the present invention, the fluid material is an anesthetic, preferably a local anesthetic.

The tubular member may have at a distal end a spring bias tending to form a distal end portion of the tubular member into an expanded anchoring configuration. This configuration is especially useful, for example, in the drainage of an abscess.

Alternatively, the tubular member may take the form of an intravenous catheter, the inner member being a needle.

Pursuant to another feature of the present invention, the tubular member, the inner member, the syringe and the needle form a modular unit and are enclosed in a sterile envelope prior to use.

A method for obtaining continued transdermal acess to a patient comprises, in accordance with the present invention, the steps of (a) puncturing a skin surface at a predetermined point with a needle, (b) injecting an anesthetic through the needle, (c) removing the needle from the skin surface and from the distal end of an instrument having a sharp distal end, (d) puncturing the skin surface at approximately the predetermined point with the sharp distal end, (e) inserting a distal end of a tubular member and the distal end of the instrument through the skin surface, and (f) removing the instrument from the patient and from the tubular member while maintaining the tubular member in a position traversing the skin surface.

Pursuant to a particular feature of the method of the present invention, the tubular member is an intravenous catheter. The method then comprises the additional step of connecting an intravenous tube to the catheter upon removal of the sharp instrument from the catheter.

Pursuant to another feature of the present invention, an assembly including the needle, tubular member, the instrument and a syringe holding the anesthetic are contained in an envelope. The method then comprises the further step of removing the assembly from the envelope prior to the puncturing of the skin surface with the needle.

Where the tubular member is an abscess drainage tube, the method also includes the step of expanding a distal end of the catheter upon an insertion of such distal end through the skin surface.

A method in accordance with the present invention for inserting a catheter into a vein or into an abscess is easier and more convenient than conventional techniques.

BRIEF DESCRIPTION OF THE DRAWING

FIG. 4 is a schematic side perspective view of the tubular member, obturator and syringe of FIG. 2, showing the syringe in a partially loaded configuration and a distal end of the obturator in an abscess.

FIG. 5 is a schematic side perspective view of the tubular member and obturator of FIGS. 2 and 4, showing an anesthetic syringe and a needle mounted to the proximal end and the distal end, respectively, of the obturator, in accordance with the present invention.

FIG. 6 is a side elevational view of the needle member of FIG. 5.

FIG. 7 is a side elevational view, on a reduced scale, of another abscess drainage device.

DETAILED DESCRIPTION

Figure 1:
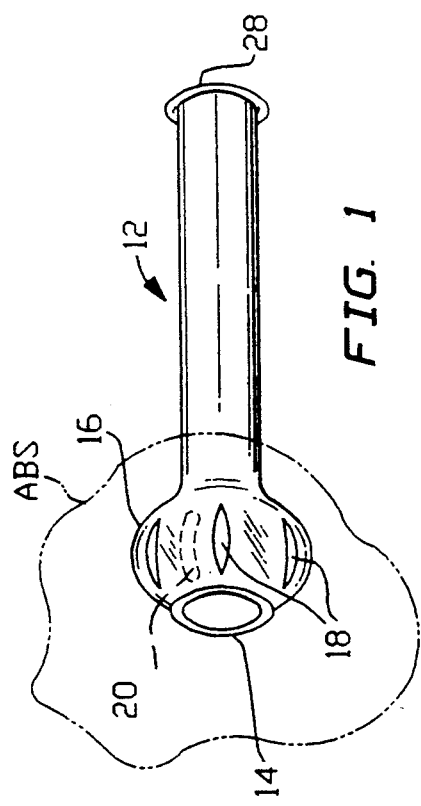
FIG. 1 is a schematic side perspective view of a flexible tubular member for use in an abscess drainage technique, showing the tubular member with a distal end portion inserted in a substantially spherical configuration inside an abscess.

As illustrated in FIG. 1, a device for use in draining an abscess ABS comprises a tubular member 12 provided at a distal end with a ring-shaped lip 14 and further provided in a distal end portion 16 with plurality of perforations in the form of longitudinal slits 18. Distal end portion 16 is made of a flexible material with a spring bias tending to form the distal end portion 16 in a substantially spherical expanded anchoring configuration, wherein slits 18 are opened, as shown in FIG. 1. Tubular abscess drainage member 12 may be provided with a radio-opaque strip 20 for facilitating a monitoring of the location of distal end portion 16 inside abscess ABS. Strip 20 can assume any shape or disposition which is effective for detection via X-ray equipment.

Figure 2:
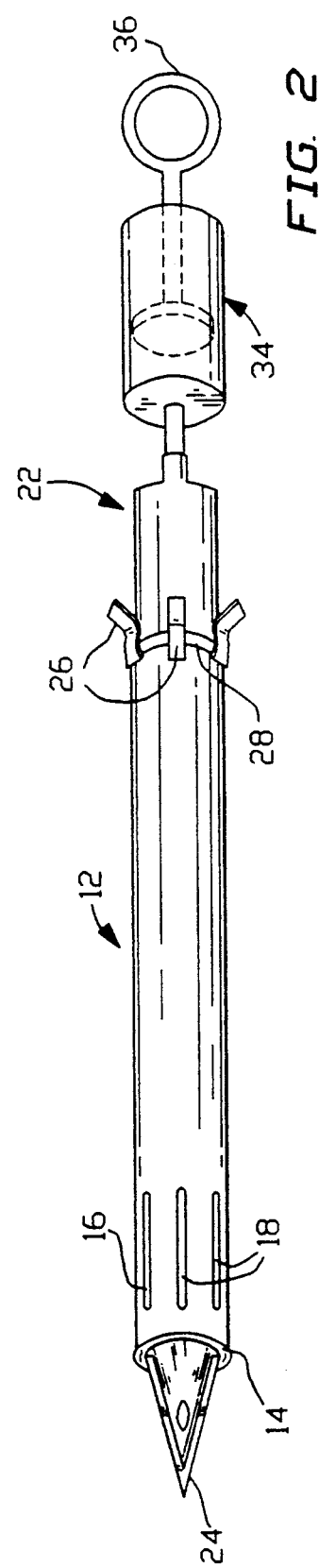
FIG. 2 is a schematic side perspective view of an abscess drainage assembly, showing the flexible tubular member of FIG. 1 mounted or locked in a stetched cylindrical configuration to a tubular obturator and further showing a syringe in an unloaded pre-use configuration.

In order to dispose distal end portion 16 of tubular member 12 inside abscess ABS, a tubular obturator 22 is inserted into the tubular member 12, as illustrated in FIG. 2. Obturator 22 has a distal end provided with a cutting edge 24 which projects from tubular member 12 through an opening defined by ring-shaped lip 14.

Figure 3:
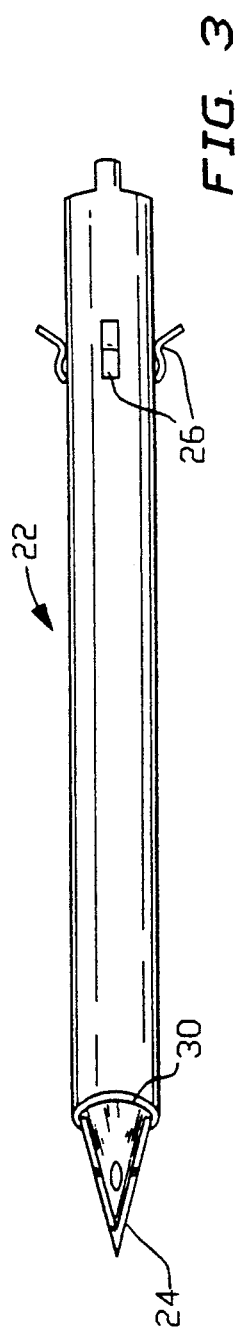
FIG. 3 is a schematic side perspective view of the tubular obturator of FIG. 2.

Prior to employment of the abscess drainage assembly illustrated in FIG. 2, tubular member 12 is locked in a stretched cylindrical configuration to obturator 22. To that end, a plurality of spring loaded locking components 26 are provided on the proximal end of obturator 22 for releasably latching onto an annular bead 28 at the proximal end of tubular member 12. Also for the purpose of temporarily locking tubular member 12 in the stretched cylindrical configuration to obturator 22, an annular shoulder 30 is provided proximally of cutting edge 24 on the obturator, as shown in FIG. 3. Ring-shaped lip 14 on tubular member 12 engages shoulder 30 to cooperate therewith and with locking components 26 to maintain tubular member 12 in the stretched cylindrical configuration.

As illustrated in FIG. 2, a syringe 34 is connected to obturator 22 at a proximal end thereof for removing a sample of fluidic material from abscess ABS. FIG. 4 shows a part of distal end portion 16 inserted into abscess ABS upon a piercing or puncturing of an overlying skin surface OSS with cutting edge 24. Upon insertion of cutting edge 24 into abscess ABS, a plunger member 36 of syringe 34 may be pulled back to apply a suction force to obturator 22, thereby drawing fluidic material from abscess ABS through the obturator 22.

If, upon obtaining a fluidic sample in syringe 34, a surgeon determines that a proper location in the abscess ABS has been found, obturator 22 is pushed further in the distal direction so that the entire distal end portion 16 of tubular member 12 is inside abscess ABS. Then, locking components 26 are actuated to release bead 28, whereupon distal end portion 16 assumes the spherical anchoring shape shown in FIG. 1 and whereupon obturator 22 is removed from tubular member 12. Tubular member 12 then remains employed in abscess ABS and continues to drain pus and other fluidic material therefrom.

As illustrated in FIGS. 5 and 6, a needle member 38 may be removably attached to the distal end of obturator 22, prior to the commencement of an abscess drainage procedure. In that event, another syringe 40 filled with a charge of a local anesthetic is connected to obturator 22 at the distal end thereof. Prior to piercing or incising with cutting edge 24 the skin tissues overlying abscess ABS, the surgeon inserts a needle 42 of needle member 38 into the abscess and presses a plunger element 44 of syringe 40 to eject the anesthetic into the infected tissues. Then, needle member 38 and syringe 40 are removed from obturator 22, syringe 34 being subsequently attached thereto.

As depicted in FIG. 7, another abscess drainage assembly comprises a flexible tubular member 52 provided at a distal end with a ring-shaped lip 54 and further provided in a distal end portion 56 with plurality of perforations in the form of longitudinal slits 58. Distal end portion 56 has a spring bias tending to form a substantially spherical configuration, thereby opening slits 58. A tubular obturator 60 is inserted into tubular member 52 and is provided at a distal end with a cutting edge 62 which projects from tubular member 52. Prior to employment of the abscess drainage assembly illustrated in FIG. 7, tubular member 52 is locked in a stretched cylindrical configuration to obturator 60. To that end, locking component 64 in the form of a pin is inserted through tubular member 52 and obturator tube 60. Also, as described hereinabove with respect to the embodiment of FIG. 2, an annular shoulder (not shown) is provided proximally of cutting edge 62 on obturator 60. Lip 54 on tubular member 52 engages the shoulder to cooperate therewith and with locking pin 64 to maintain tubular member 52 in the stretched cylindrical configuration.

Figure 8:
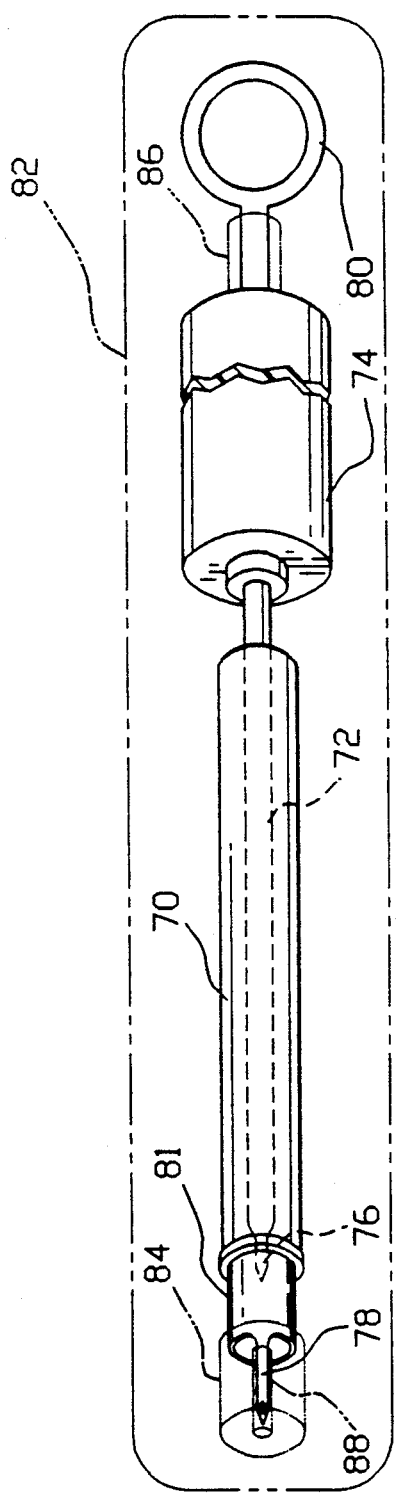
FIG. 8 is a schematic side elevatinal view of a catheterization assembly in accordance with the present invention.

As illustrated in FIG. 8, an assembly for obtaining continued transdermal access to a patient and, more particularly, for use in inserting a tubular intravenous catheter 70 comprises a hollow inner member in the form of a needle 72 inserted into the catheter and a syringe 74 connected to needle 72 at a proximal end thereof. As is customary, needle 72 has a sharp distal end 76 which can project from catheter 70. A second needle 78 is removably attached to catheter 70 at the distal end thereof, whereby an ejection stroke of syringe plunger 80 ejects fluid material such as a local anesthetic from syringe 74 through needle 72 and out along needle 78. Secondary needle 78 is removably attached to catheter 70 and/or needle 72 via a cup-shaped collar connector 81.

Catheter 70, needle 72, syringe 74 and needle 78 form a modular unit and are enclosed in a sterile envelope 82 prior to use. In the envelope 82, a protective cap 84 is disposed over needle 78, while a slotted sleeve 86 is disposed about plunger 80 to prevent an untimely ejection stroke thereof. Protective cap 84 may be provided internally with a tube 88 which receives needle 78.

In a method for obtaining continued transdermal acess to a patient, the modular unit comprising catheter 70, needle 72, syringe 74 and needle 78 is removed from envelope 82. Protective cap 84 and slotted sleeve 86 are removed from around needle 78 and plunger 80, respectively. A skin surface of a patient (not shown) is then punctured or pierced at a predetermined point with needle 78. Plunger 80 is then pushed in the proximal direction to inject an anesthetic through needle 72 and needle 78, thereby preparing the dermal tissues for receiving larger needle 72 and the still larger catheter 70. Upon a removal of needle 78 from the skin surface and from the distal end of needle 72 and catheter 70, the skin surface is punctured at approximately the same location with the sharp distal end 76 of needle 72. Distal end 76 of needle 72 and the distal end of catheter 70 are then advanced through the skin surface. Subsequently, needle 72 is extracted from the patient and from catheter 70, while maintaining the catheter is maintained in a position traversing the skin surface. Subsequently, an intravenous tube (not shown) is connected to catheter 70.

It is to be noted that tubular member 12 is also a catheter for purposes of the invention.

Although the invention has been described in terms of particular embodiments and applications, one of ordinary skill in the art, in light of this teaching, can generate additional embodiments and modifications without departing from the spirit of or exceeding the scope of the claimed invention. It is to be noted, for example, that radio-opaque strip 20 can serve in the guidance of tubular member 12 and obturator 22 during in insertion or employment operation. Thus, abscesses which are located deep inside a patient may be drained by tubular member 12 or 52.

Accordingly, it is to be understood that the drawings and descriptions herein are proferred by way of example to facilitate comprehension of the invention and should not be construed to limit the scope thereof.

What is claimed is:

1. A method for obtaining continued transdermal access to a patient, comprising the steps of:
   providing an instrument having a sharp distal end and a needle attached to said instrument at said sharp distal end, said needle being different from said sharp distal end;
   providing a tubular member having a distal end;
   puncturing a skin surface at a predetermined point with said needle;
   injecting an anesthetic through said needle;
   removing said needle from said skin surface and from the distal end of said instrument;
   subsequently to the removal of said needle from the distal end of said instrument, puncturing said skin surface at approximately said predetermined point with said sharp distal end;
   inserting the distal end of said tubular member and the distal end of said instrument through said skin surface, said tubular member surrounding said instrument during said step of inserting; and
   removing said instrument from the patient and from said tubular member while maintaining said tubular member in a position traversing said skin surface.

2. The method defined in claim 1 wherein said tubular member is an intravenous catheter.

3. The method defined in claim 2, further comprising the step of connecting an intravenous tube to said catheter upon removal of said instrument from said catheter.

4. The method defined in claim 2 wherein an assembly including said needle, tubular member, said instrument and a syringe containing said anesthetic are contained in an envelope, further comprising the step of removing said assembly from said envelope prior to said step of puncturing.

5. The method defined in claim 1 wherein said tubular member is an abscess drainage tube, further comprising the step of expanding a distal end of said tubular member upon an insertion of such distal end through said skin surface.

6. A device for obtaining continued transdermal access to a patient, comprising:
   a tubular member;
   a hollow inner member inserted into said tubular member, said inner member having a sharp distal end projecting from said tubular member;
   a syringe connected to said inner member at a proximal end thereof, said syringe containing a fluid material; and
   a needle different form said sharp distal end and removably attached to one of said tubular member and said inner member at a distal end thereof, whereby an ejection stroke of said syringe ejects said fluid material from said syringe through said inner member and out along said needle.

7. The device defined in claim 1 wherein said fluid material is an anesthetic.

8. The device defined in claim 7 wherein said tubular member has a distal end portion with a spring bias tending to form said distal end portion into an expanded anchoring configuration.

9. The device defined in claim 7 wherein said tubular member is an intravenous catheter and said inner member is a needle.

10. The device defined in claim 9, further comprising an envelope enclosing said tubular member, said inner member, said syringe and said needle.

11. The device defined in claim 6 further comprising an envelope enclosing said tubular member, said inner member, said syringe and said needle.

* * * * *

UNITED STATES PATENT AND TRADEMARK OFFICE
CERTIFICATE OF CORRECTION

PATENT NO. : 5,282,788
DATED : February 1, 1994
INVENTOR(S) : Peter J. Wilk and Naomi L. Nakao It is certified that error appears in the above-indentified patent and that said Letters Patent is hereby corrected as shown below:

Claim 7, line 1, change "claim 1" to --claim 6--.

Signed and Sealed this

Twenty-sixth Day of July, 1994

Attest:

BRUCE LEHMAN

*Attesting Officer*  *Commissioner of Patents and Trademarks*